US00PP35511P3

(12) United States Plant Patent
Nakagoshi et al.

(10) Patent No.: US PP35,511 P3
(45) Date of Patent: Nov. 28, 2023

(54) BUNASHIMEJI MUSHROOM NAMED 'HKHM25'

(50) Latin Name: *Hypsizygus marmoreus*
Varietal Denomination: HKHM25

(71) Applicant: HOKUTO CORPORATION, Nagano (JP)

(72) Inventors: Ayumi Nakagoshi, Nagano (JP); Aya Seki, Nagano (JP); Chiaki Goto, Nagano (JP)

(73) Assignee: HOKUTO CORPORATION, Nagano (JP)

( * ) Notice: Subject to any disclaimer, the term of this patent is extended or adjusted under 35 U.S.C. 154(b) by 183 days.

(21) Appl. No.: 17/803,159

(22) Filed: Mar. 8, 2022

(65) Prior Publication Data

US 2022/0304209 P1 Sep. 22, 2022
US 2023/0148465 P4 May 11, 2023

(51) Int. Cl.
*A01H 15/00* (2006.01)

(52) U.S. Cl.
USPC ..... Plt./394
CPC ..... *A01H 15/00* (2013.01)

(58) Field of Classification Search
USPC ..... Plt./394
See application file for complete search history.

*Primary Examiner* — Annette H Para
(74) *Attorney, Agent, or Firm* — Taro Yaguchi

(57) ABSTRACT

The present variety of Bunashimeji mushroom named 'HKHM25' was cultivated by the gathering and repeated breeding of Bunashimeji mushrooms having thick and elastic stems, dark cap color, strong cap roll, and a large mushroom size, has a high quality and enhanced cultivation stability. This edible mushroom is exquisite in stability, reproducibility and uniformity when being produced.

25 Drawing Sheets

BACKGROUND OF THE INVENTION

This invention relates to a new and distinct variety of Bunashimeji mushroom, *Hypsizygus marmoreus* (Peck) H.E.Bigelow. This new variety named 'HKHM25', cultivated by repeated breeding of Bunashimeji mushroom having thick and elastic stems, dark cap color, strong cap roll, and a large mushroom size, has a high quality and enhanced cultivation stability, and ensures presentable stability, reproducibility, and uniformity.

The annual production of Bunashimeji mushrooms is approximately 120,000 tons in 2020, making it the second most consumed edible mushroom after enokitake mushroom in Japan. However, since Bunashimeji mushrooms have become available in large quantities in the market, Bunashimeji mushrooms with improved flavor, quality and shelf life has been pursued, which led to the development of 'Hokuto 18gokin' by our company. Further, our company has been conducting a wide variety of studies for the more stable cultivation and better quality of Bunashimeji mushrooms. Our company has developed a 'marmo22go' mushroom which is thicker, whiter, and has larger mushroom than 'Hokuto 18gokin'.

Further, using 'marmo22go' as a parent, as a result of continuing breed improvement by cross breeding to improve stability and quality, 'HKHM25', which has thicker stems and stronger cap roll, as compared to 'marmo22go', was developed, confirming its stability, reproducibility, and uniformity.

SUMMARY OF THE INVENTION

The present invention is a new and distinct variety of mushroom plant characterized particularly by having thick and elastic stems, dark cap color, strong cap roll, and a large mushroom size, which can be cultivated by gathering and repeated breeding of fungal strains having a stability, reproducibility and uniformity when being produced. This novel and distinct variety of mushroom is identified as 'HKHM25'.

DETAILED DESCRIPTION OF THE INVENTION

'HKHM25' has been asexually reproduced by tissue culture, at HOKUTO CORPORATION in Japan. The history of the 'HKHM25' mushroom in terms of improvement period and the like are set forth in the following chronological list of each stage of variety improvement:

December 2014: Cultivation of 'MH025615' strain.

January 2017: Cultivation of 'M11025617' ('marmo22go') strain.

December 2019: 'MH025615' and 'MH025617' ('marmo22go') strains were crossed and a strain with thick stem, strong cap roll, and good quality among the obtained strains was selected as 'MH025633'. We then repeated the cultivation test to distinguish the strains.

March 2021: After repeated cultivation tests, since distinguishability, stability, and uniformity were confirmed, the strain was named 'HKHM25' and its cultivation was completed. Applied for registration of a new variety to the Ministry of Agriculture, Forestry and Fisheries of Japan.

Figure 1:
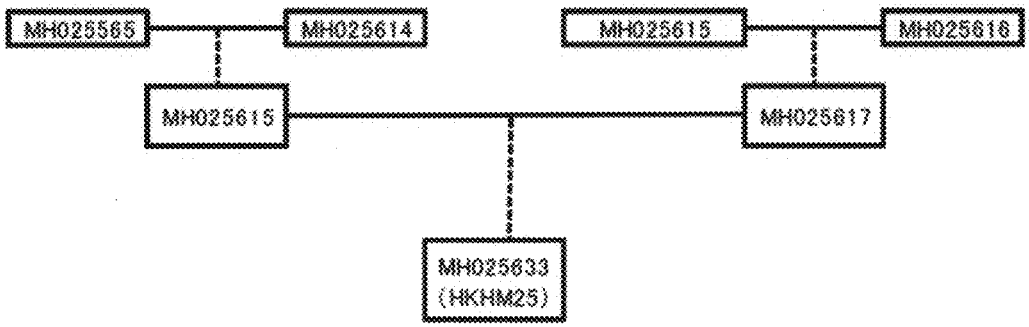
FIG. 1 shows a phylogenetic tree illustrating the antecedents of 'HKHM25'.

The above crossing is summarized in the phylogenetic tree illustrated in FIG. 1.

The 'HKHM25' mushroom has the following characteristics: thick and elastic stems, dark cap color, strong cap roll, and overall large size.

(1) Comparison with Existing Variety by Dual Culture

Dual culture was performed for the 'HKHM25' mushroom and a similar variety to examine whether or not a zone line is formed.

Study Method:

As an examination method, a potato dextrose agar medium was used, and the 'HKHM25' mushroom and the similar variety were inoculated thereon face to face at an interval of 3 cm, and then culture was performed at 25° C. for 28 days to examine whether or not a zone line was formed.

Strains used for the comparison between present variety, 'HKHM25' and other varieties:

'HKHM25': Present variety

'Hokuto 18gokin': Variety similar to the present variety

'marmo22go': Parent variety of the present variety

Figure 2A:
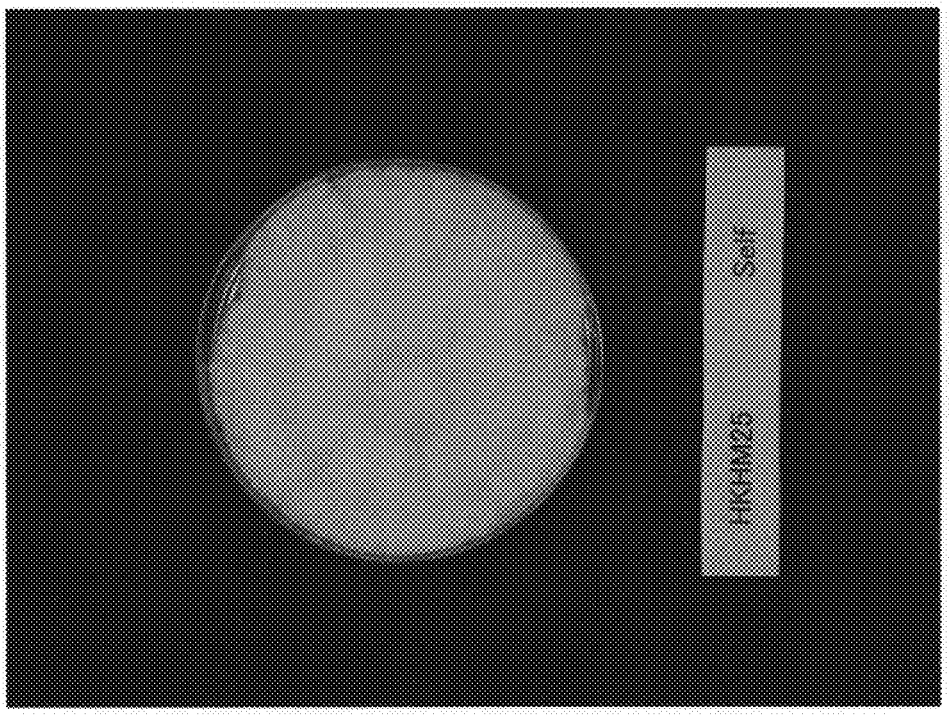
FIGS. 2A and 2B respectively show front and back images of a dual-culture of 'HKHM25'.
Figure 2B:
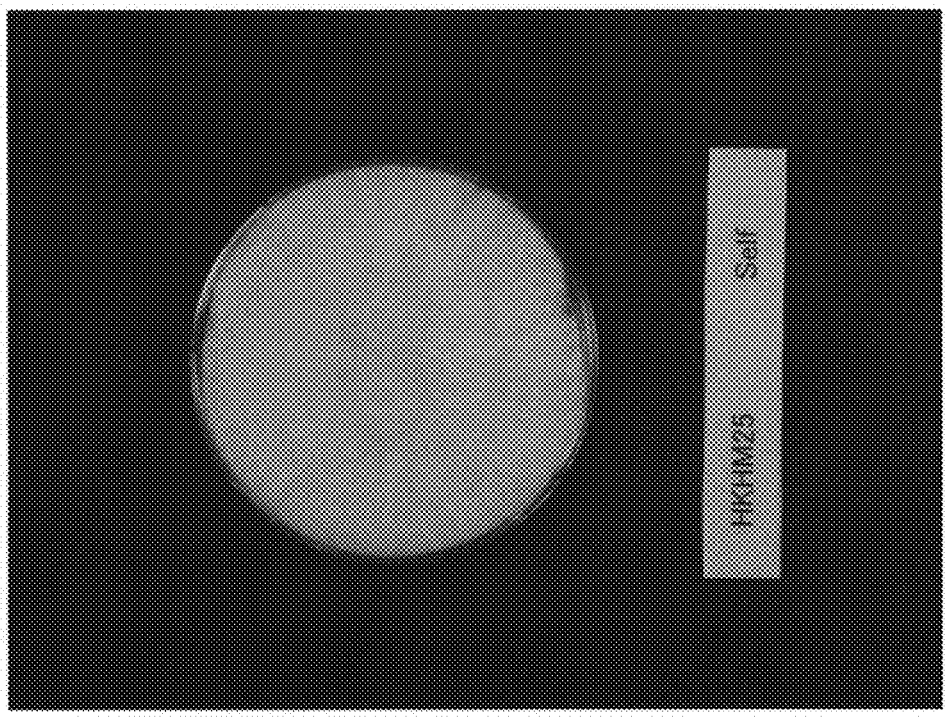
Figure 3A:
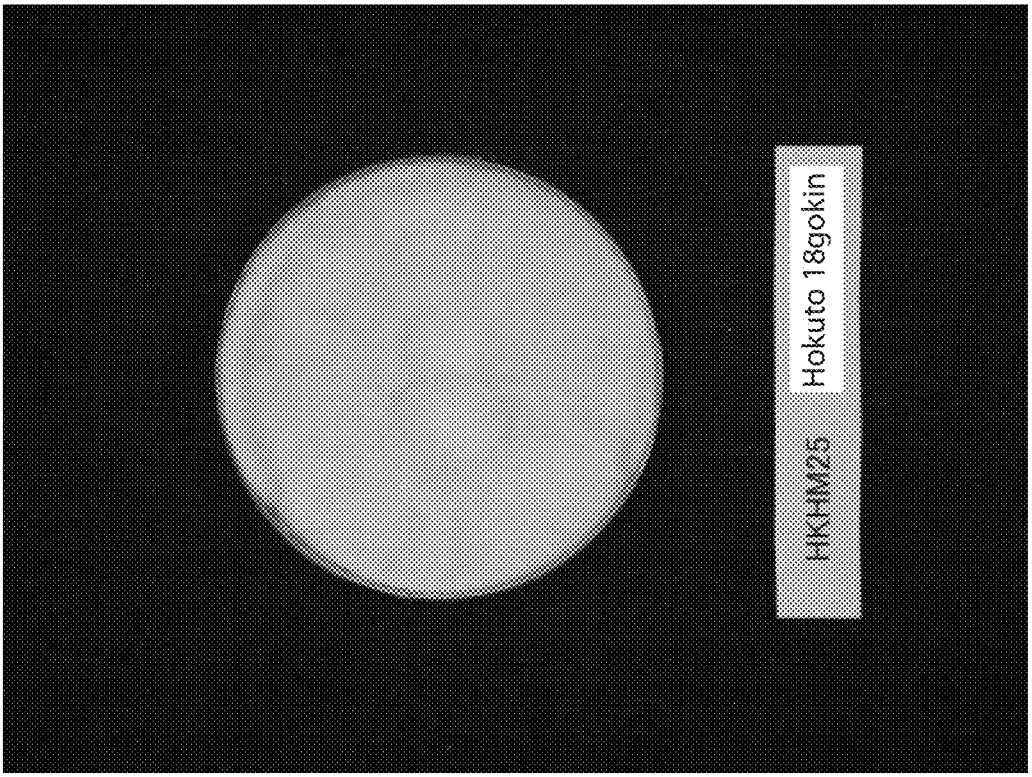
FIGS. 3A and 3B respectively show front and back images of a dual-culture of 'HKHM25' and 'Hokuto 18gokin'.
Figure 3B:
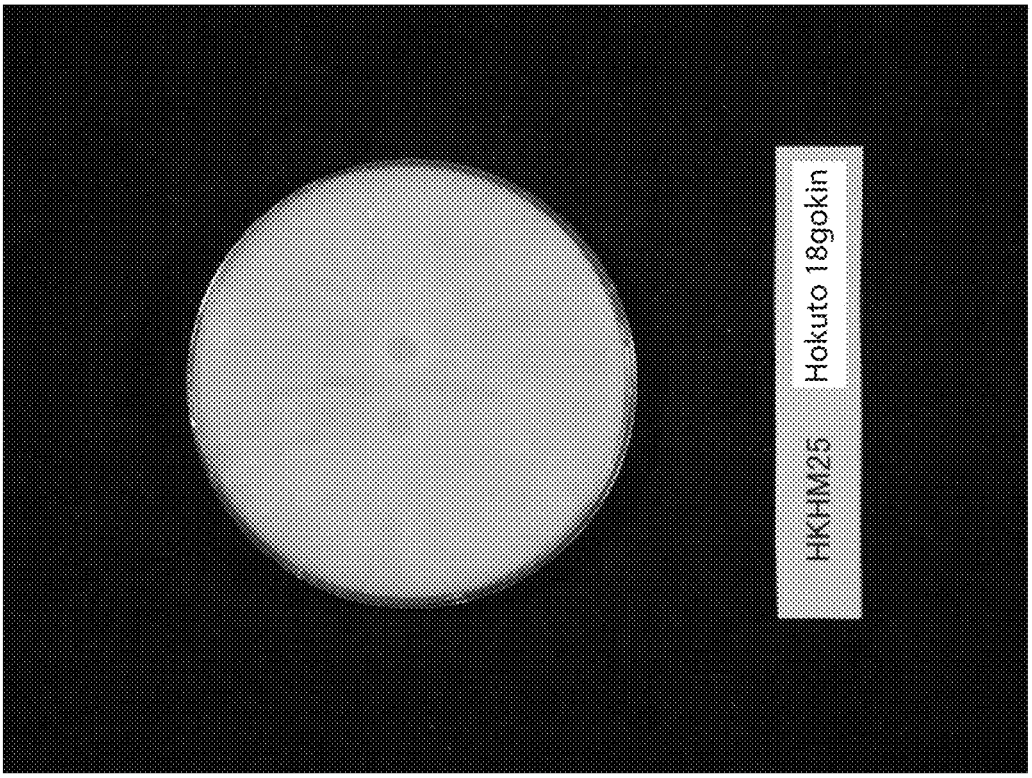
Figure 4A:
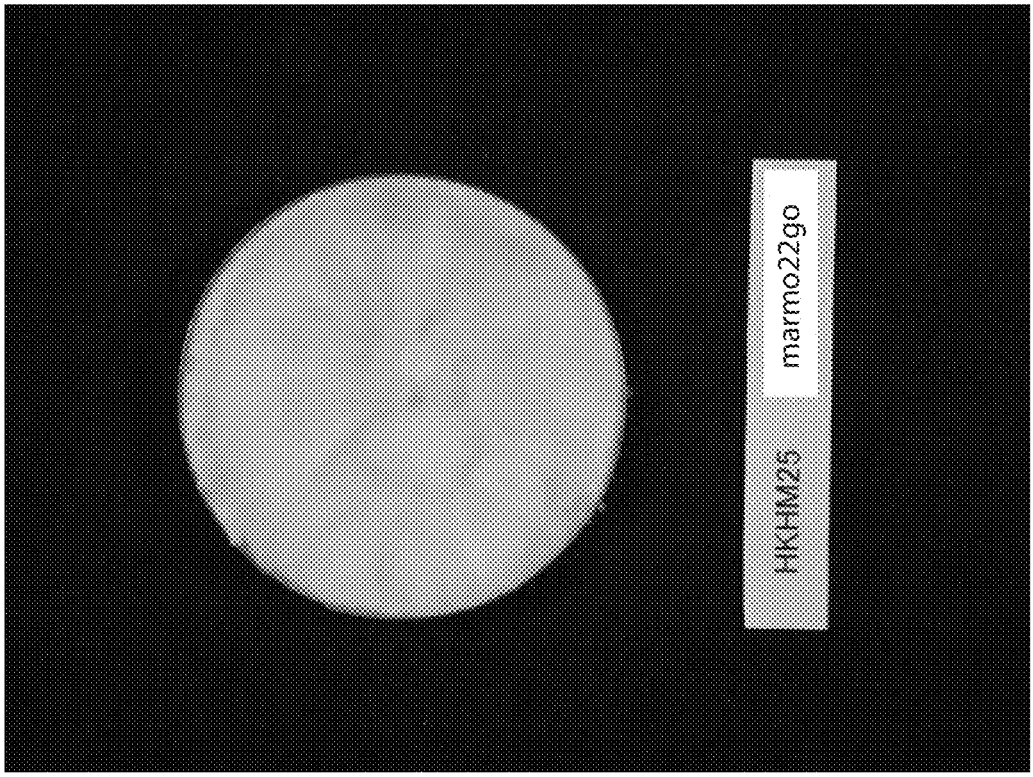
FIGS. 4A and 4B respectively show front and back images of a dual-culture of 'HKHM25' and 'marmo22go'.
Figure 4B:
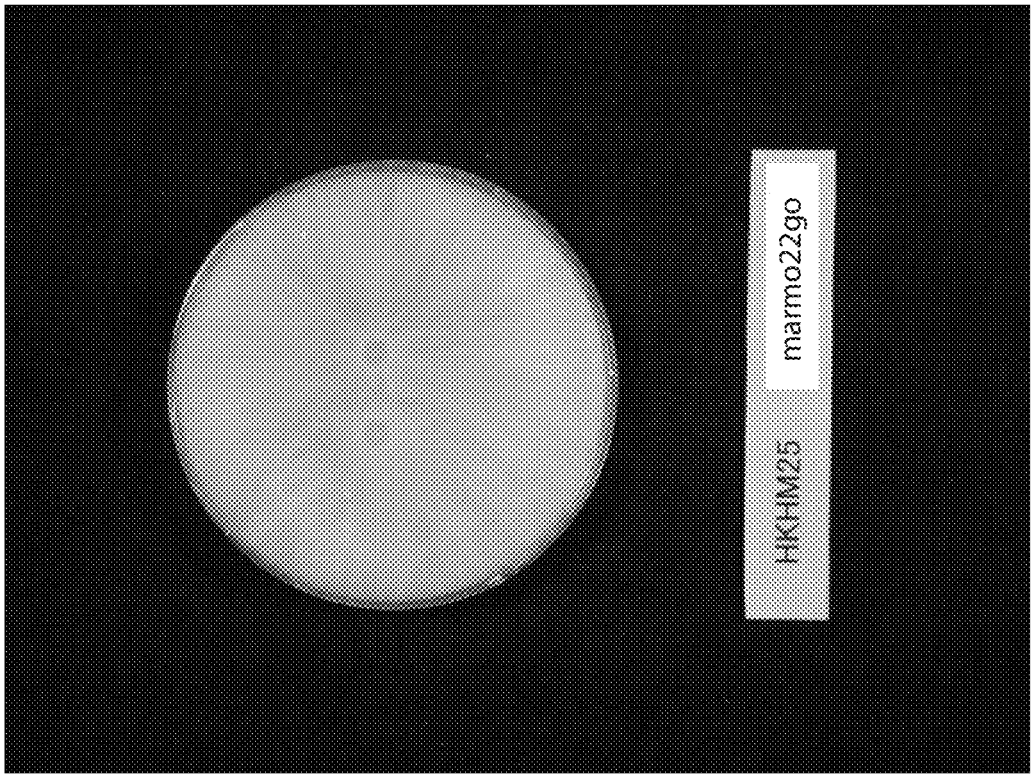
Figure 5A:
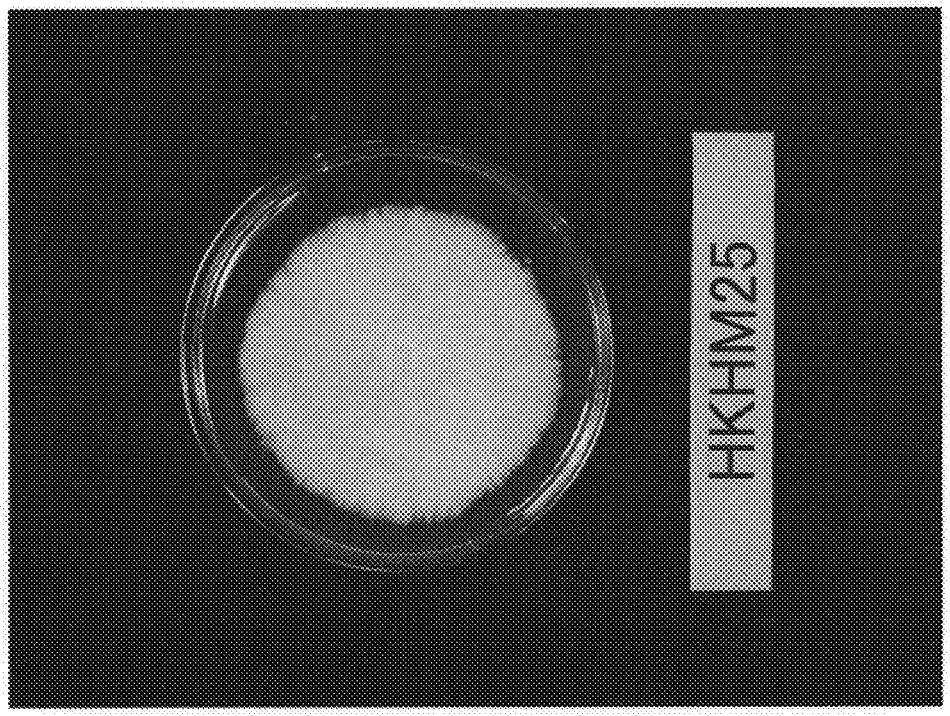
FIGS. 5A and 5B respectively show front and back images of a fungal flora of 'HKHM25' grown in a petri dish.
Figure 5B:
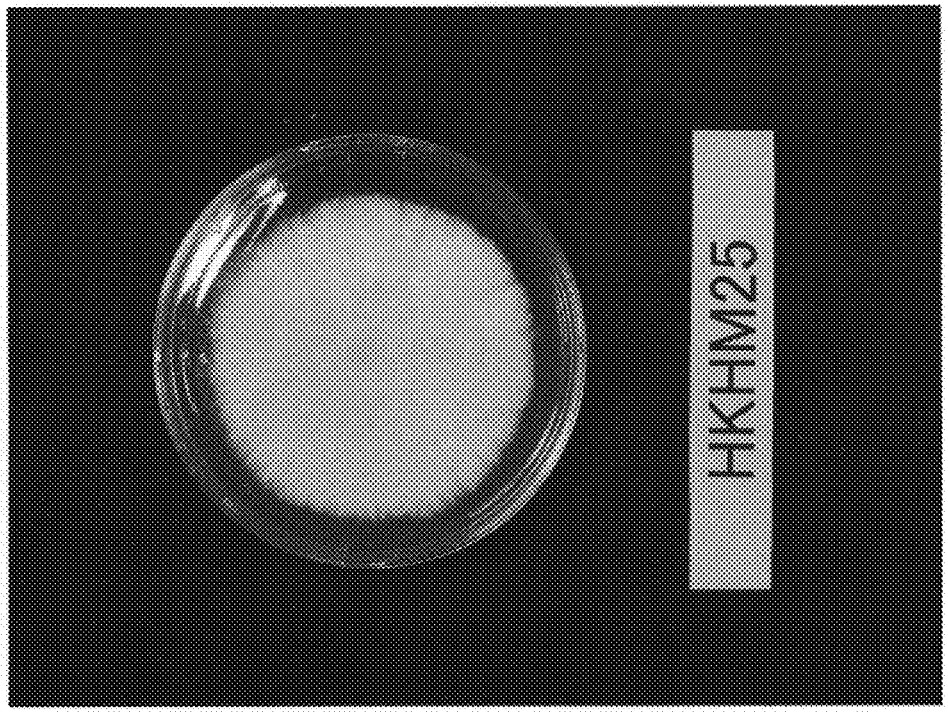
Figure 6A:
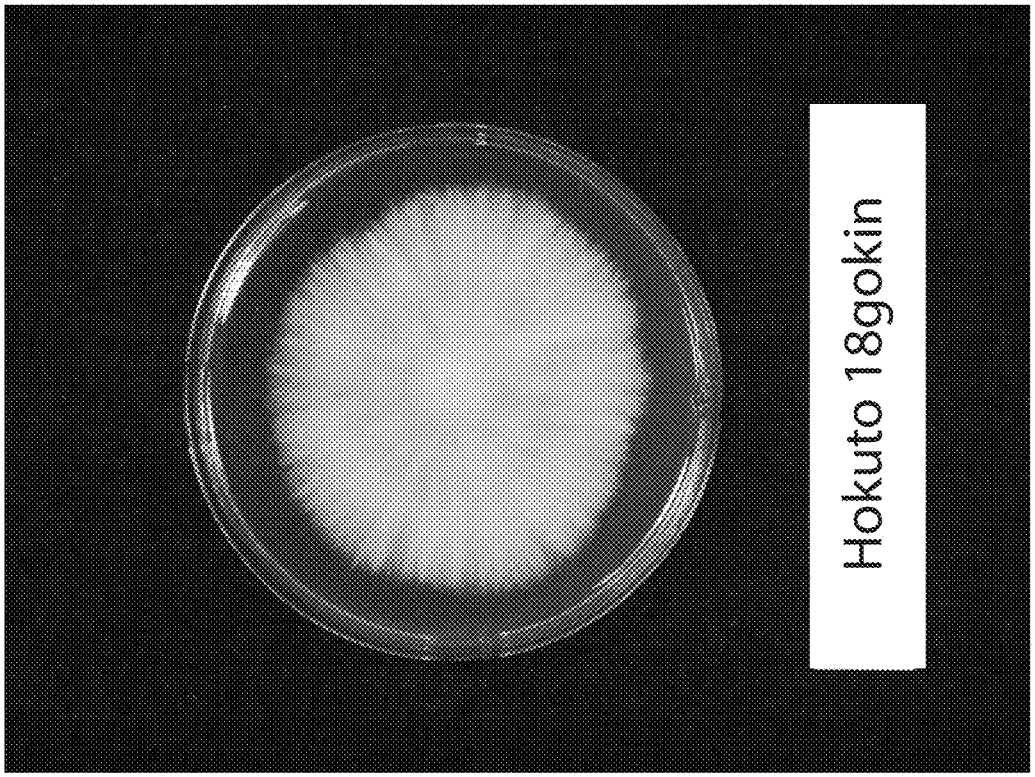
FIGS. 6A and 6B respectively show front and back image of a fungal flora of 'Hokuto 18gokin' grown in a petri dish.
Figure 6B:
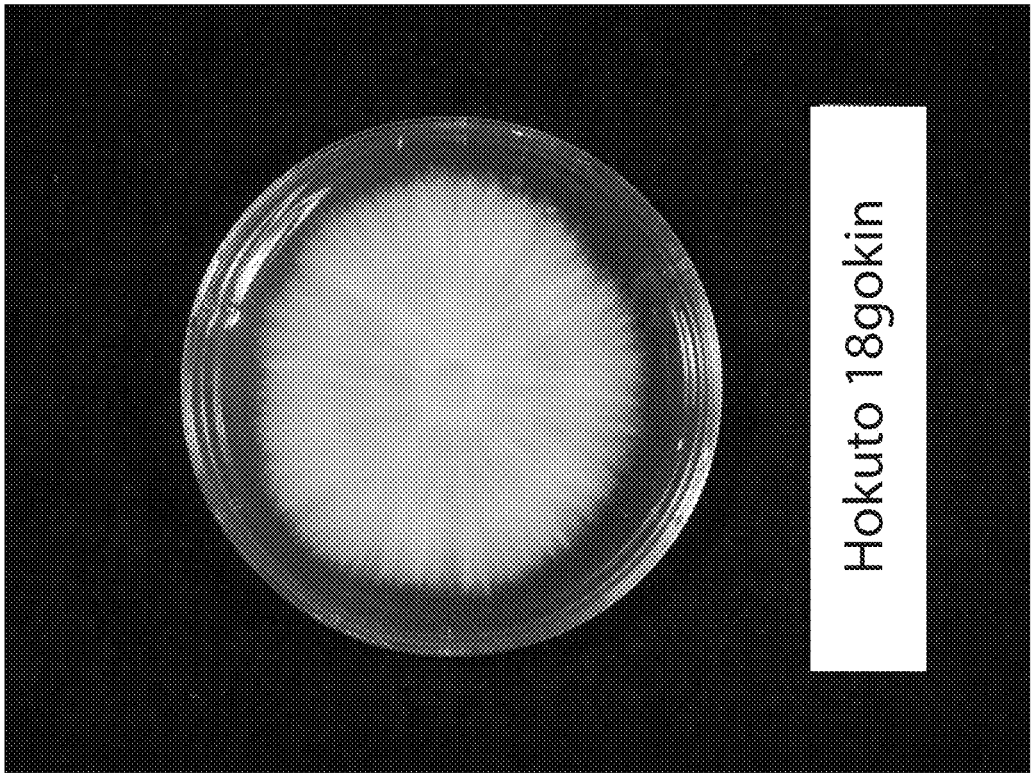
Figure 7A:
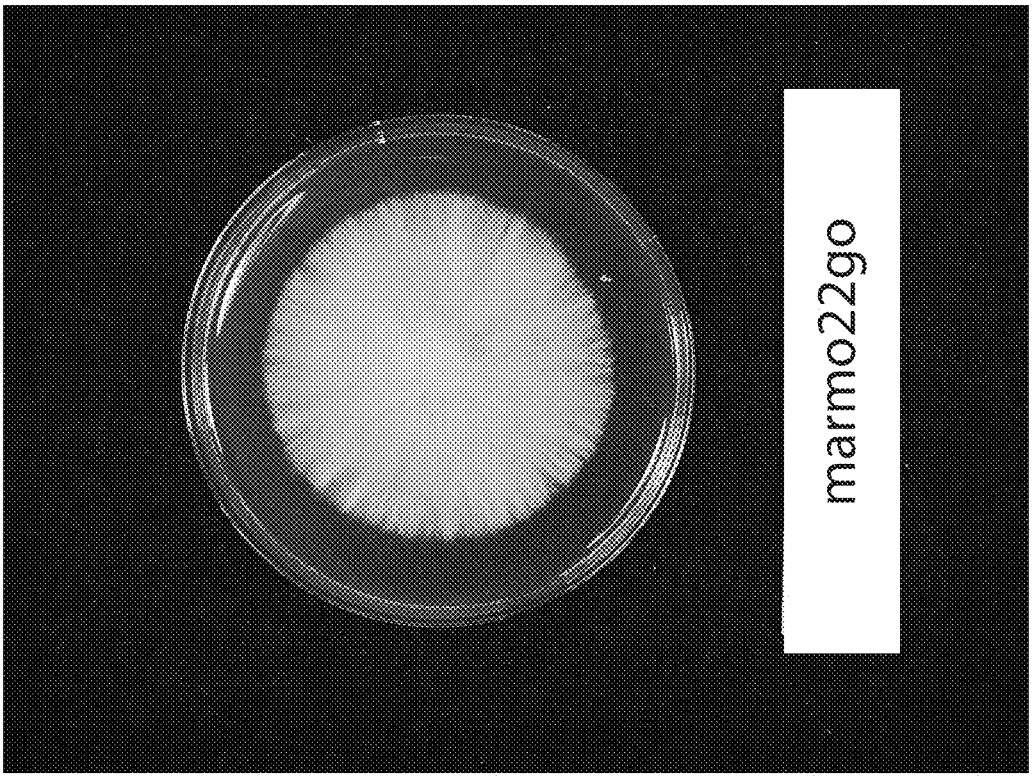
FIGS. 7A and 7B respectively show front and back images of fungal flora of 'marmo22go' grown in a petri dish.
Figure 7B:
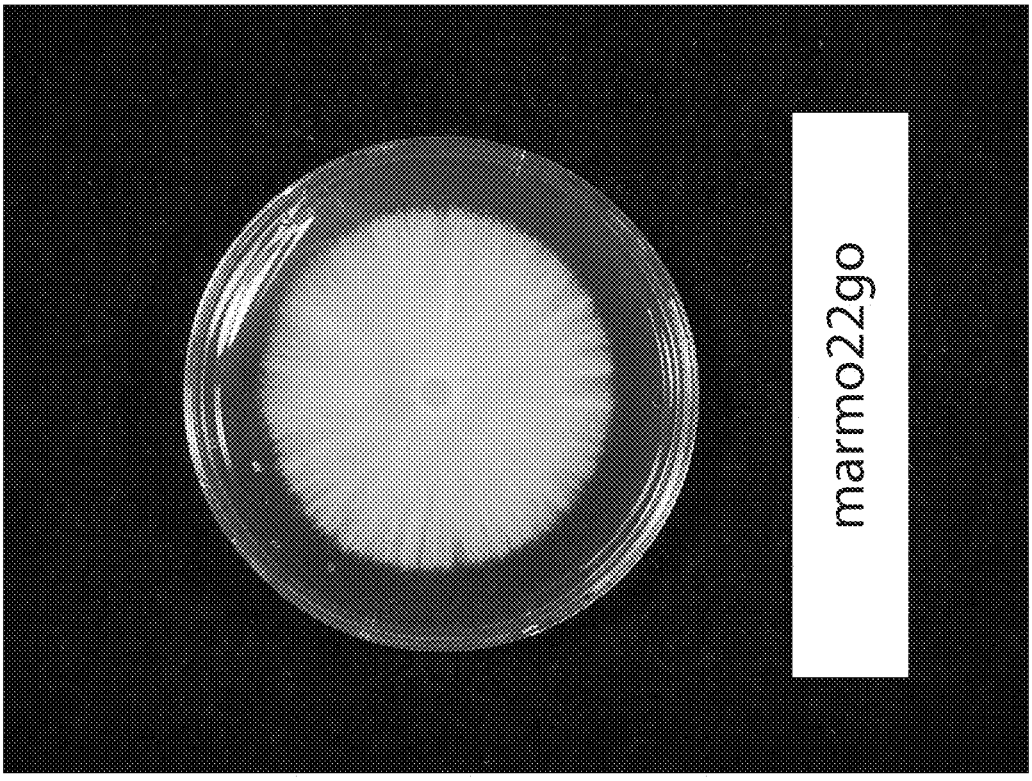
Figure 8:
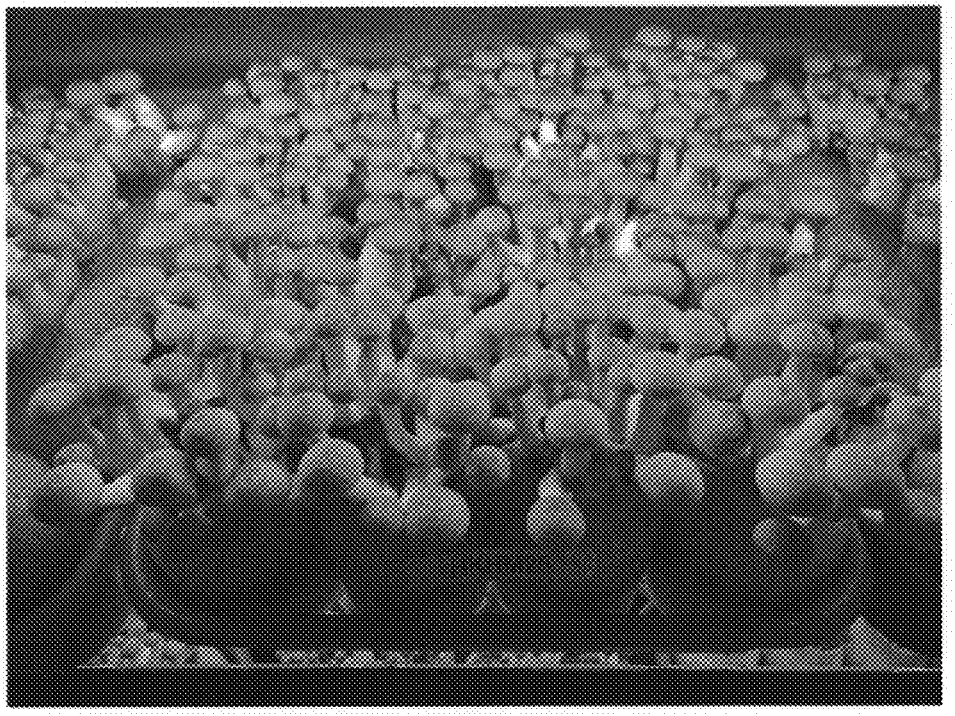
FIG. 8 shows an image of cultivation area of 'HKHM25'.
Figure 9:
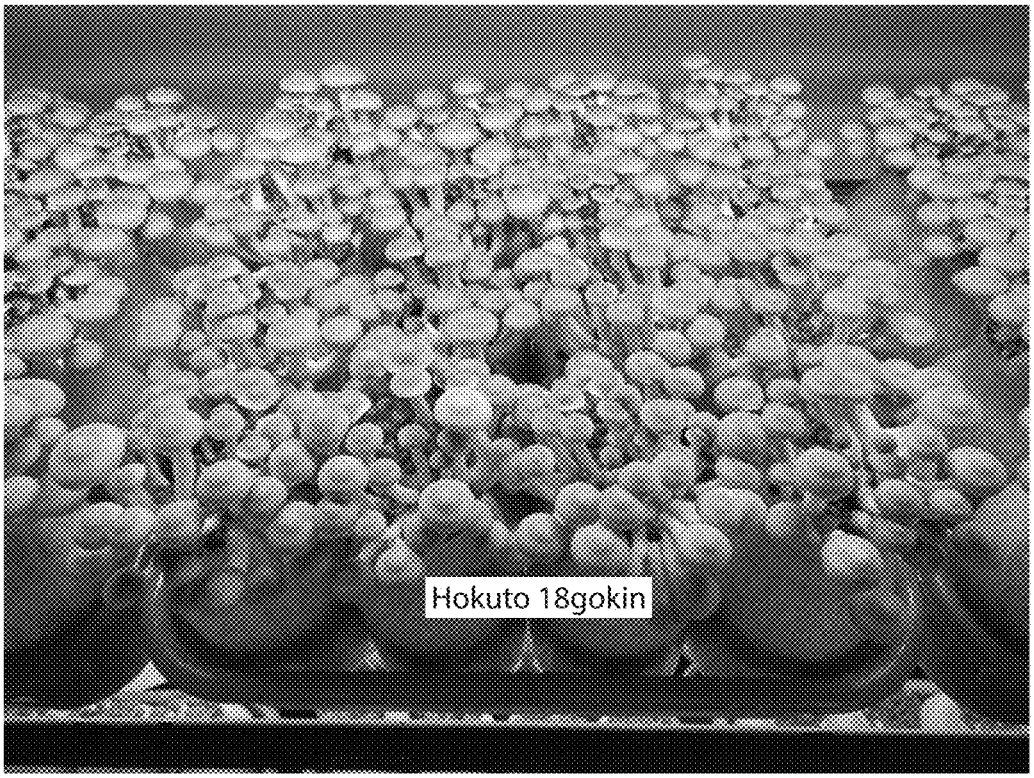
FIG. 9 shows an image of cultivation area of 'Hokuto 18gokin'.
Figure 10:
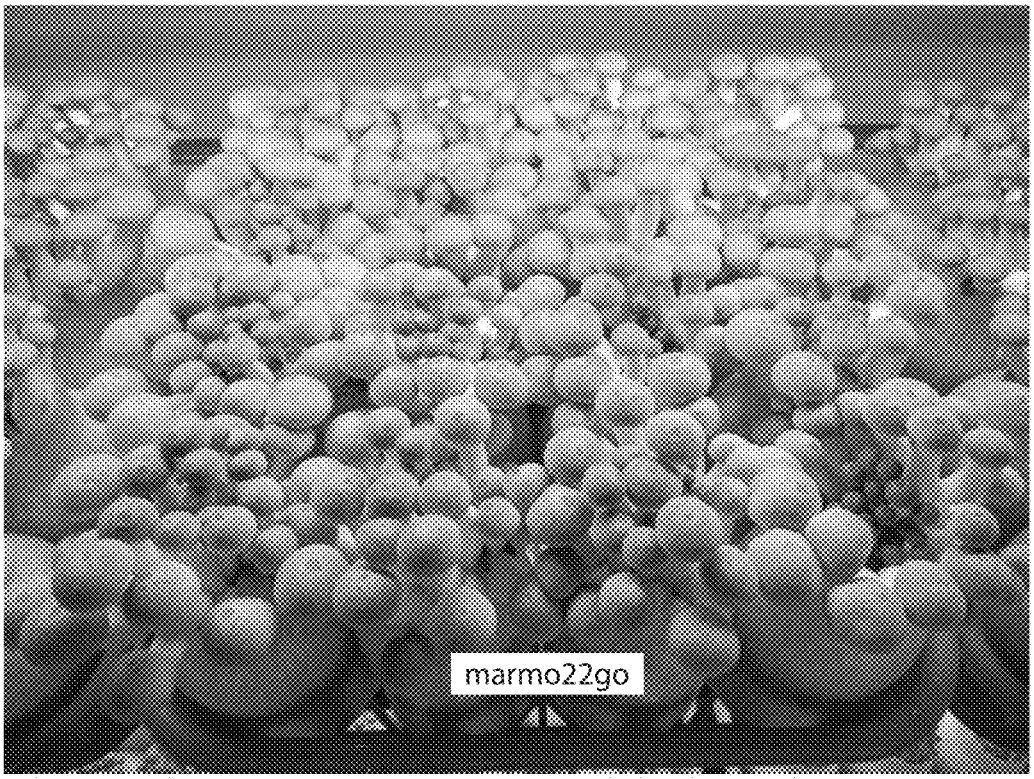
FIG. 10 shows an image of cultivation area of 'marmo22go'.
Figure 11:
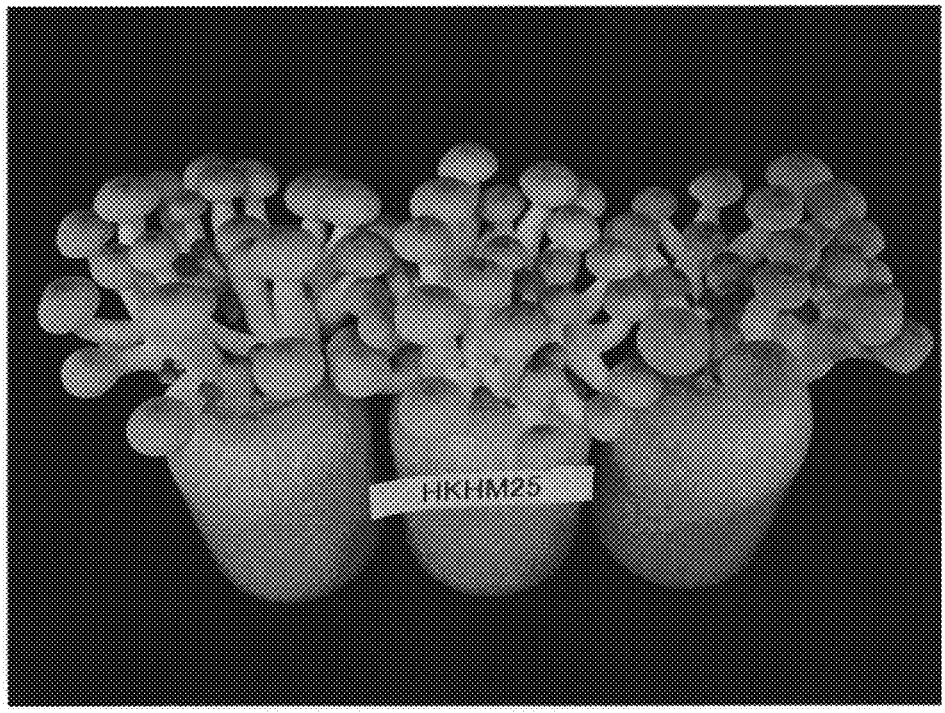
FIG. 11 shows an image of a fruit body of 'HKHM25'.
Figure 12:
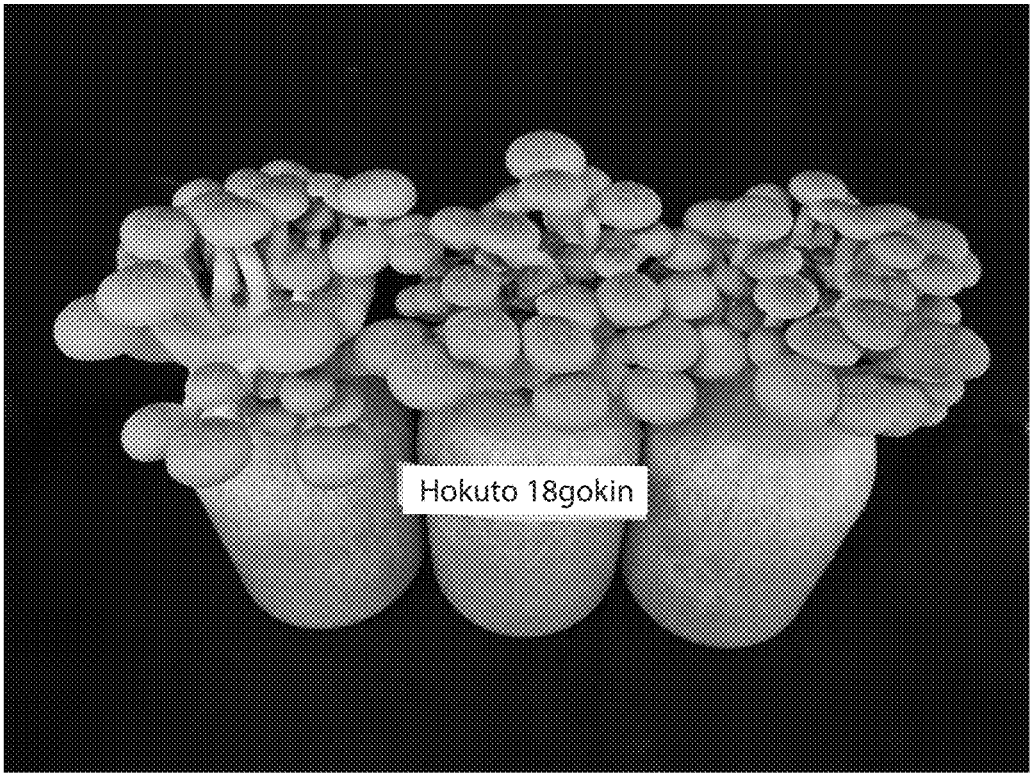
FIG. 12 shows an image of a fruit body of 'Hokuto 18gokin'.
Figure 13:
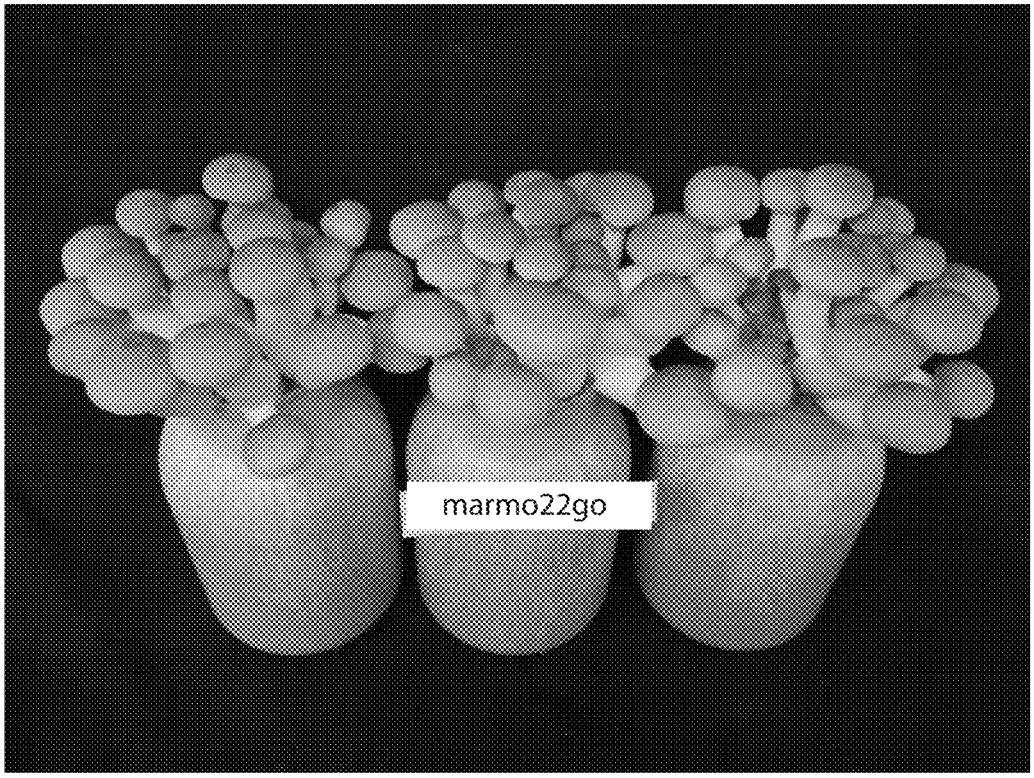
FIG. 13: shows an image of a fruit body of 'marmo22go'.
Figure 14:
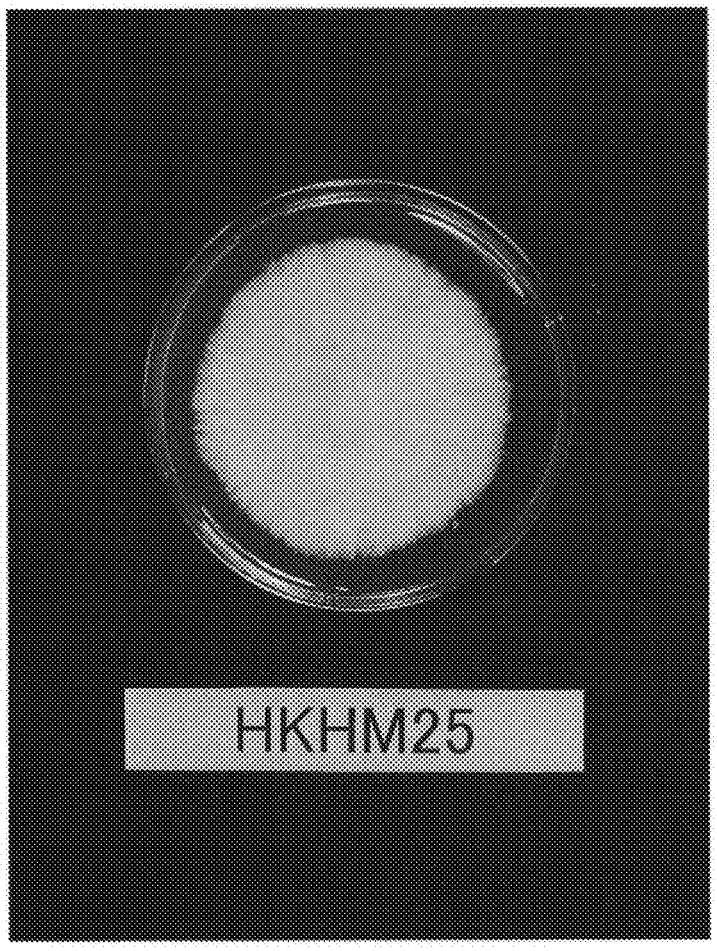
FIG. 14 shows an image of density and surface color of fungal flora in cultured hyphae of 'HKHM25'.
Figure 15:
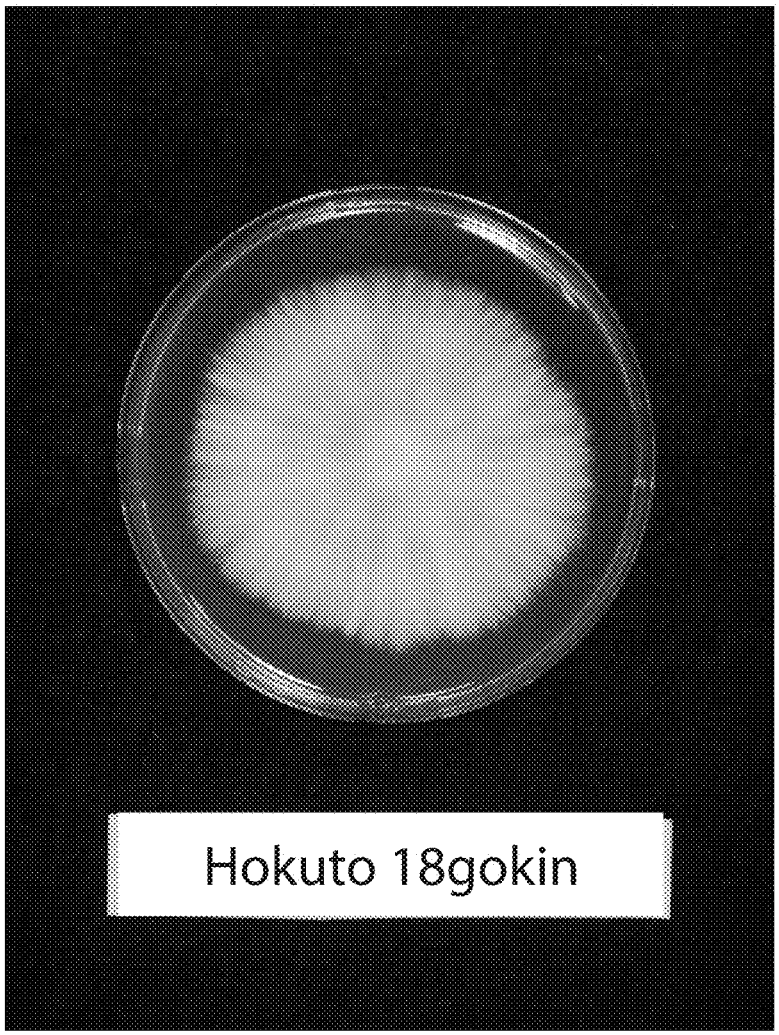
FIG. 15 shows an image of density and surface color of fungal flora in cultured hyphae of 'Hokuto 18gokin'.
Figure 16:
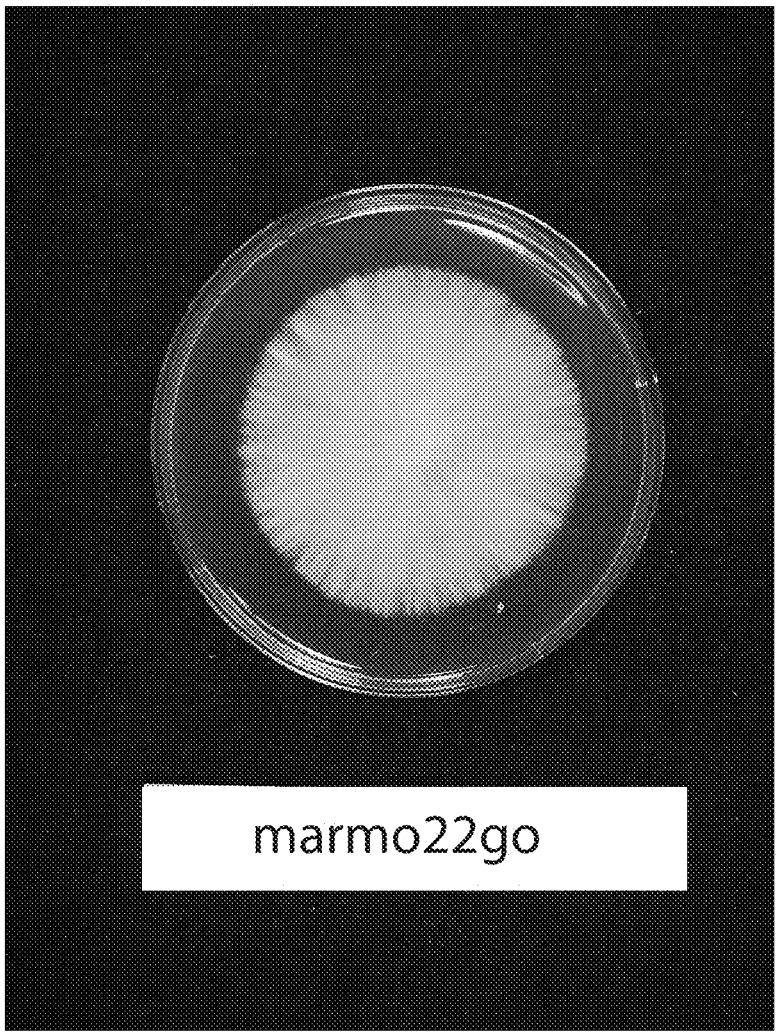
FIG. 16 shows an image of density and surface color of fungal flora in cultured hyphae of 'marmo22go'.
Figure 17:
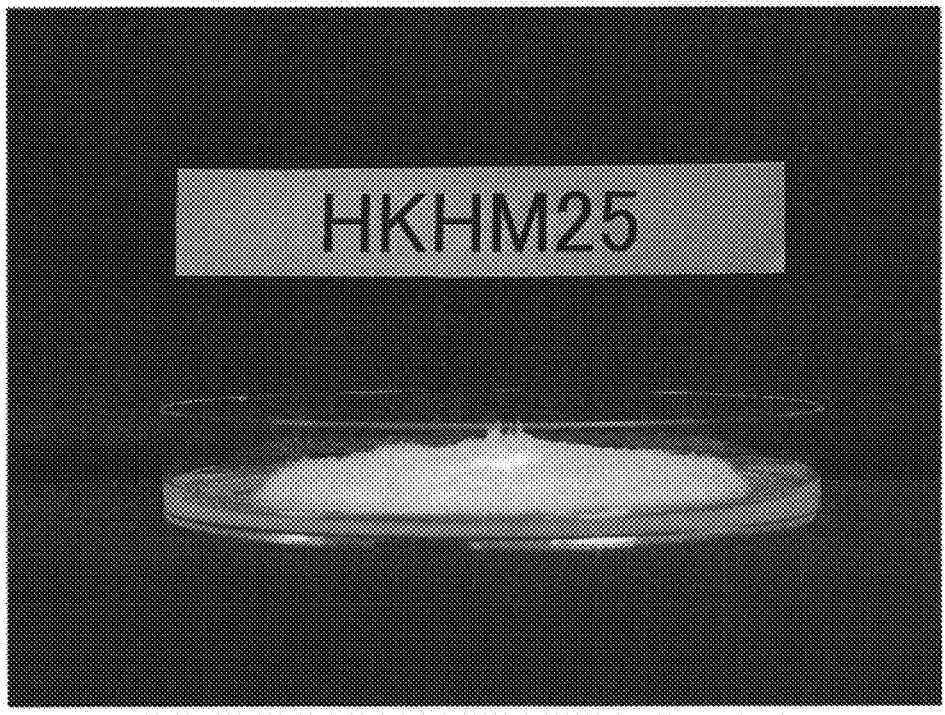
FIG. 17 shows an image of development of aerial hypha of 'HKHM25'.
Figure 18:
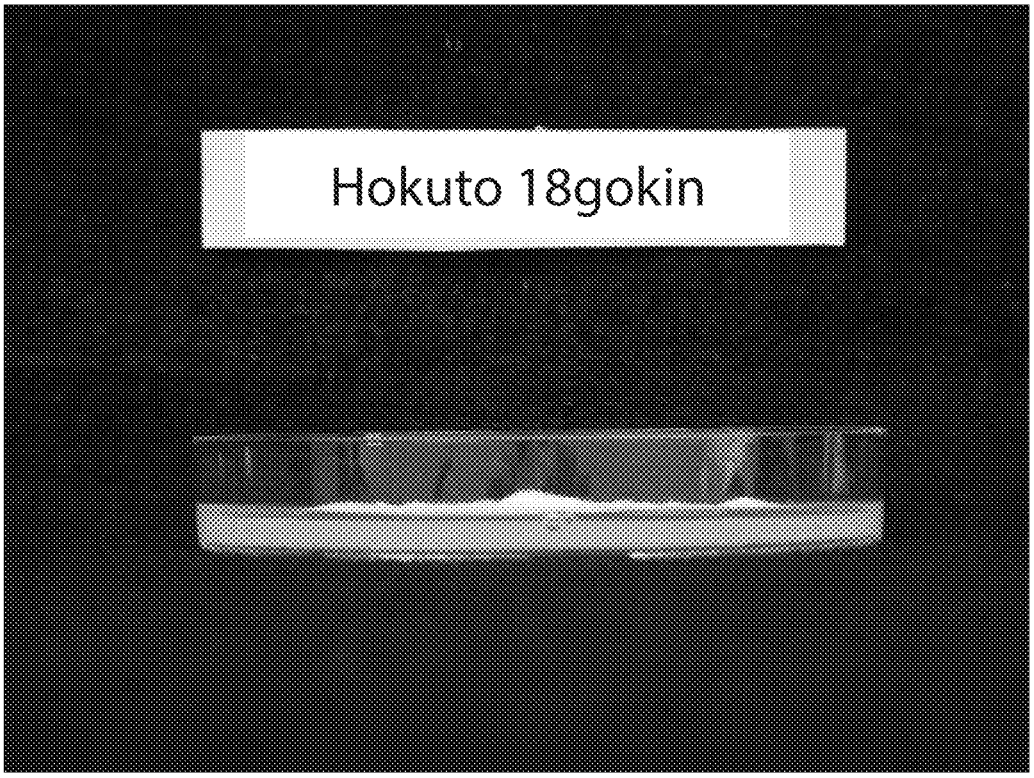
FIG. 18 shows an image of development of aerial hypha of 'Hokuto 18gokin'.
Figure 19:
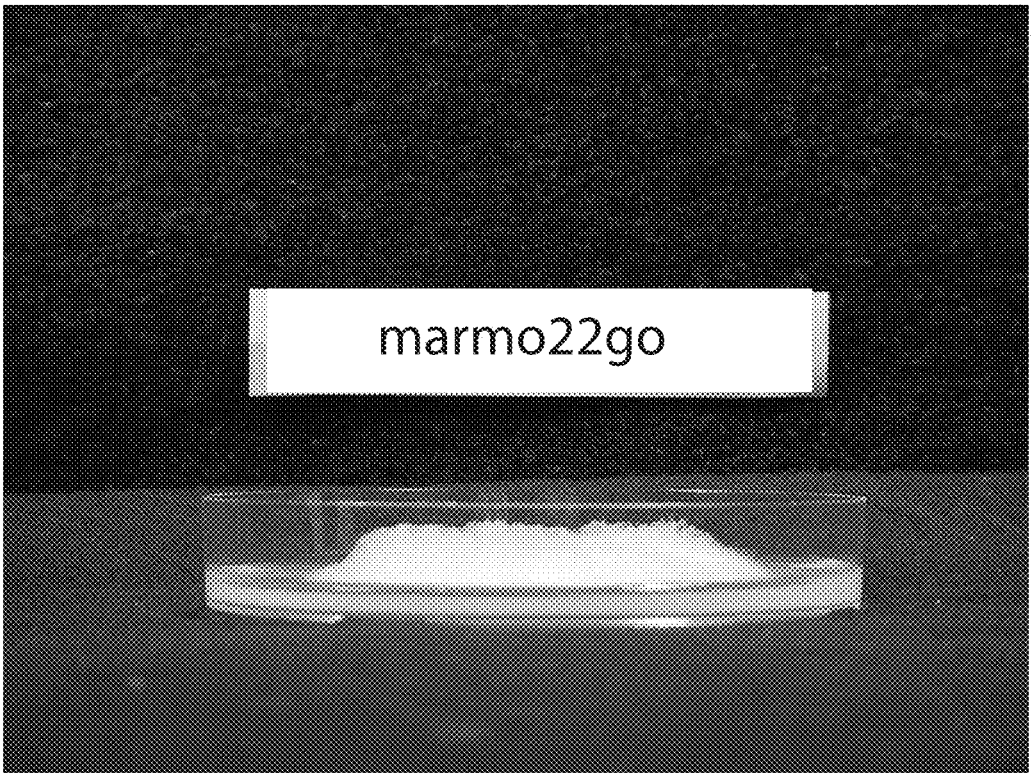
FIG. 19 shows an image of development of aerial hypha of 'marmo22go'.
Figure 20:
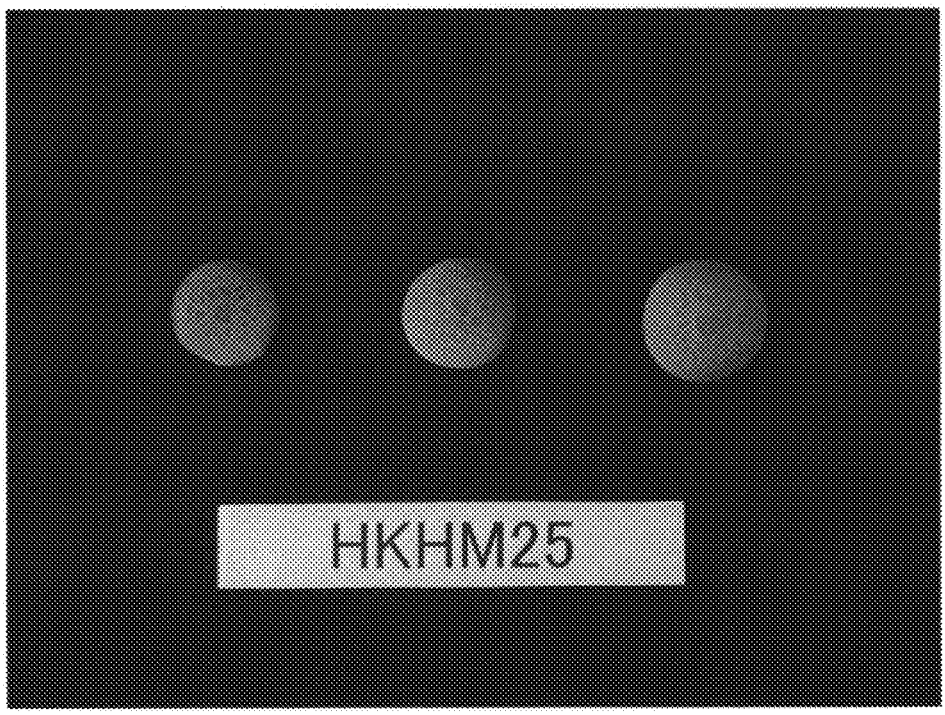
FIG. 20 shows an image of size and distribution of mottle of 'HKHM25'.
Figure 21:
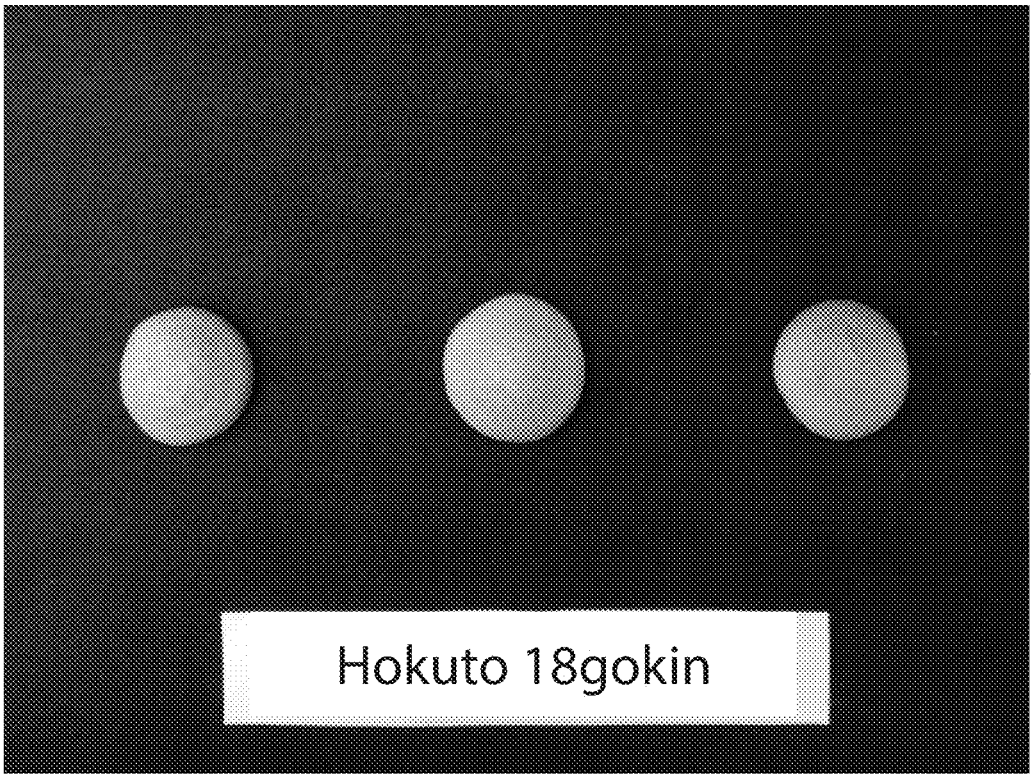
FIG. 21 shows an image of size and distribution of mottle of 'Hokuto 18gokin'.
Figure 22:
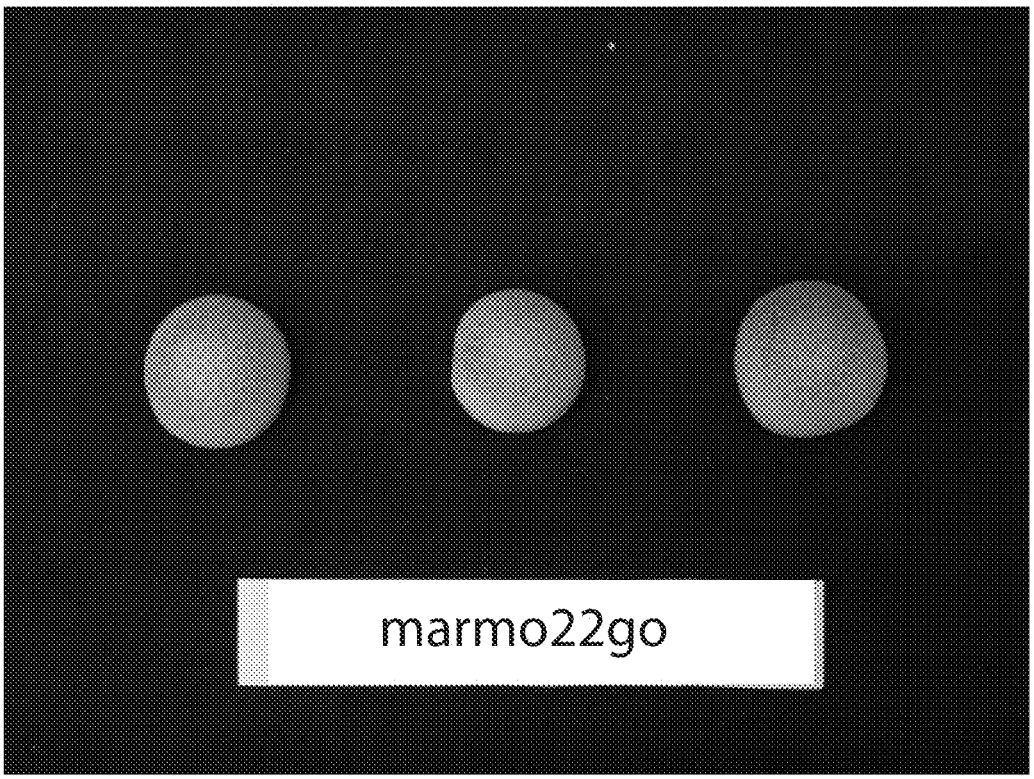
FIG. 22 shows an image of size and distribution of mottle of 'marmo22go'.
Figure 23:
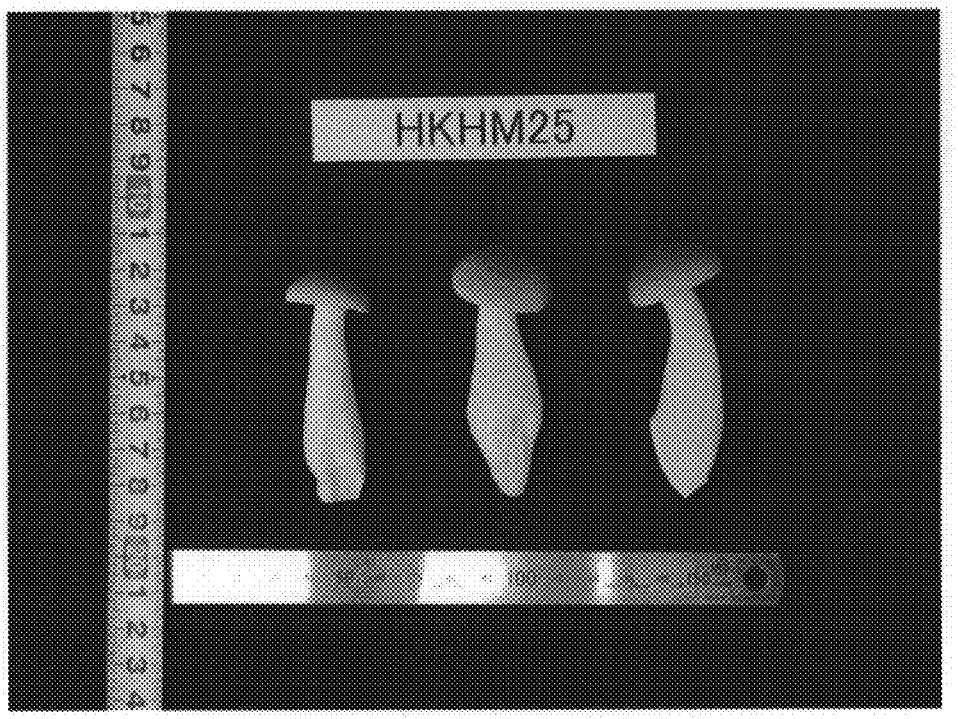
FIG. 23 shows an image of shape and thickness of stipe of 'HKHM25'.
Figure 24:
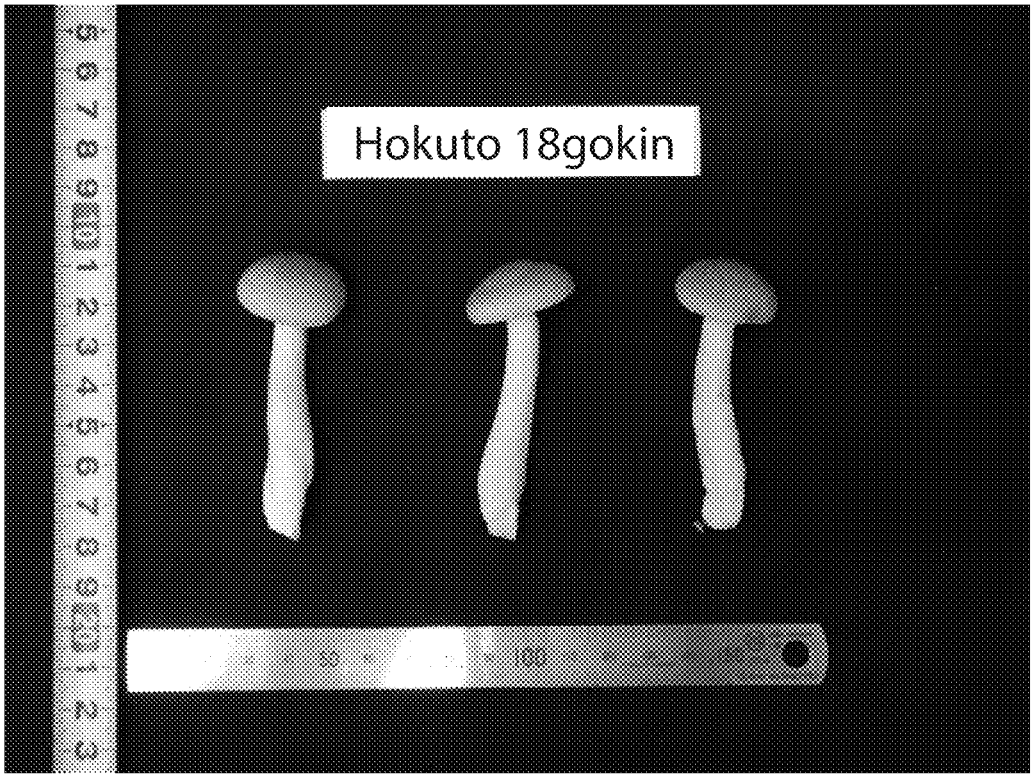
FIG. 24 shows an image of shape and thickness of stipe of 'Hokuto 18gokin'.
Figure 25:
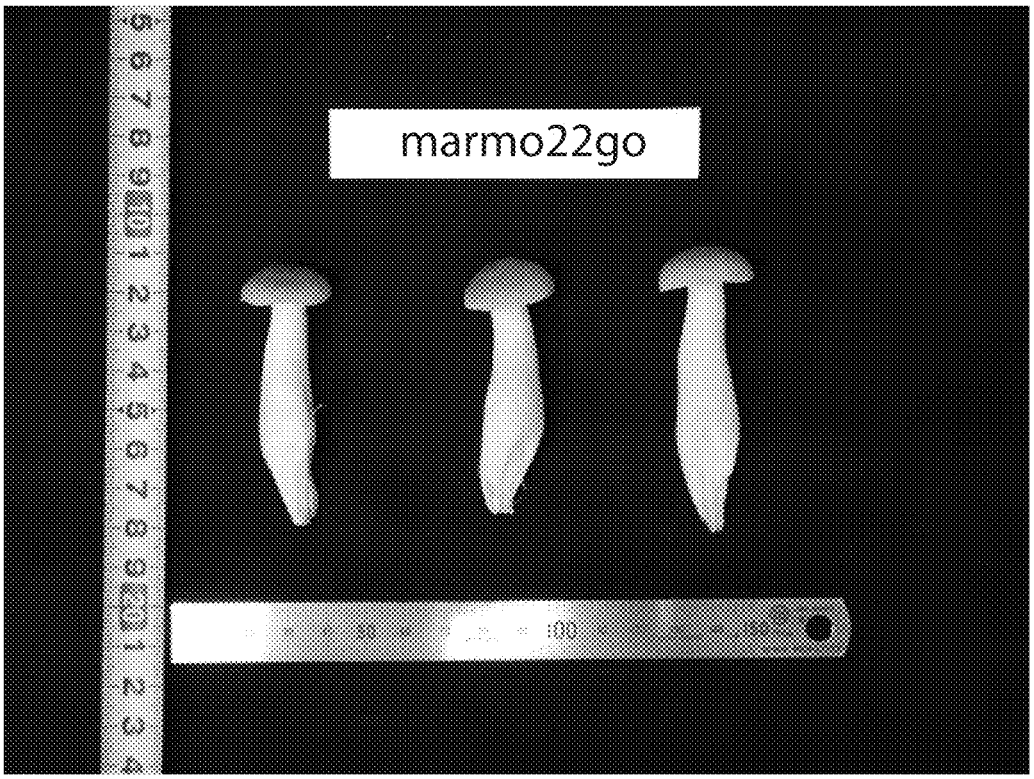
FIG. 25 shows an image of shape and thickness of stipe of 'marmo22go'.

Results:

Zone lines were formed between 'HKHM25' and all other co-cultured varieties (TABLE 1, FIGS. 2 to 4)

This clearly shows that the present mushroom is a new variety.

| | Similar varieties | |
|---|---|---|
| | Hokuto 18gokin | marmo22go |
| HKHM25 | + | + |

+ is present and − is absent.

*Zone line formation was not observed in the dual culture between 'HKHM25' strains.

(2) Growth Characteristics of 'HKHM25'

Study Method:

After inoculating an agar piece of the 'HKHM25' having a diameter of 5 mm and an agar piece of the similar variety having a diameter of 5 mm on a potato dextrose agar medium, preculture was performed at 25° C. for 4 days so as to make the regeneration of hyphae equal (about 10 mm in diameter), and then culture was performed for 7 days at intervals of 5° C. between 5° C. and 30° C. An average daily hyphae growth rate was calculated based on a hyphae growth rate for 7 days of the culture. Also, the optimum culture period for 'HKHM25' is 80 days, and the number of growing days at that time is 23.1 days.

Results:

'HKHM25' had the fastest average daily hyphae growth rate at 20° C. In addition, HKHM25 had slower mycelial growth rate than 'Hokuto 18gokin' and 'marmo22go' at each temperature zone (Table 2).

(3) Morphological Characteristics of the 'HKHM25' Mushroom in a Cultivation Example Cultivation Method:

Container: An 850 polypropylene bottle (Capacity: 850 ml, diameter 58 mm) was used.

Culture medium: Conifer sawdust, corn cob, rice bran and wheat bran were mixed at the dry weight ratio of 7:3:8:2, and the water content was adjusted to 65%. The culture medium was filled up to the brim of the bottle at the rate of 540±20 g per bottle, and was sterilized at high pressure.

Starter culture: About 20 ml of sawdust starter cultures per bottle was inoculated.

Culture: Culture was performed at 22° C. for 50 to 90 days at 70% moisture.

Growth: After completing the culture, the inoculum is removed, and shifted to a growing room. Development was conducted under a temperature of 15±1° C., at humidity of 95% or about 2,000 ppm $CO_2$ density. Also, light was not particularly irradiated until the first 14th day, then irradiated with about 500 to 1,000 Lx. The mushroom is harvested when the cap in the center of the stump has sufficiently opened.

Cultivation Results:

Table 2 shows the characteristics of the 'HKHM25' and specific difference in characteristics as compared with the similar variety when culture was performed under the abovementioned conditions.

In addition, according to R.H.S. Colour Chart, the color of the central part of cap: 199A, the color of the peripheral area of cap: 199C, the color of gill: 158C, the color of stripe: 155B. All color references are from The R.H.S. Colour Chart of The Royal Horticultural Society of London (R.H.S.), fifth edition published in 2007. Also, the descriptions are from mushrooms that are on the 24$^{th}$ day.

TABLE 2

Fungus characteristics Table of *Hypsizygus marmoreus* (Peck) H.E. Bigelow of Recording and Registration
(Please circle the applicable items for the characteristics.)

| Character | Characteristic values of present variety (comparison with standard varieties) 01 | 02 | 03 | 04 | 05 | 06 | 07 | 08 | 09 | Remarks (Measured values, etc.) | Characteristic values of similar varieties (marmo22go) | (Hokuto 18gokin) |
|---|---|---|---|---|---|---|---|---|---|---|---|---|
| Physiological property | | | | | | | | | | | | |
| Dual culture | | | | | | | | | | | | |
| Zone line formation | none | | | | | | | | observed | — | 09 | 09 |
| Dislike-touch reaction | none | | | | | | | | observed | — | 01 | 01 |
| Density of cultured hyphae | low | medium | high | | | | | | | 03 | 02 | 02 |
| Development of aerial hypha | low | medium | high | | | | | | | 03 | 03 | 02 |
| Color of surface of fungal flora | white | light yellow | pale yellow | | | | | | other | 02 | 01 | 01 |
| Color of back of fungal flora | white | light yellow | pale yellow | | | | | | other | 02 | 02 | 02 |
| Accommodativeness for temperature | | | | | | | | | | | | |
| Optimal temperature for hyphal growth | | | 20~22° C. | | 24~26° C. | | 28~30° C. | | | 03 21.9° C. | 05 24.1° C. | 04 22.5° C. |
| Hyphal growth rate 5° C./mm | | | low | | medium | | high | | | 05 0.52 mm | 06 0.70 mm | 05 0.56 mm |
| Hyphal growth rate | | | | | | | | | | | | |
| 10° C./mm | | | low | | medium | | | | | 04 0.86 mm | 05 1.16 mm | 05 1.24 mm |
| 15° C./mm | | | low | | medium | | high | | | 05 1.65 mm | 05 1.95 mm | 05 1.80 mm |
| 20° C./mm | | | low | | medium | | high | | | 04 2.47 mm | 05 2.79 mm | 05 2.60 mm |
| 25° C./mm | | | low | | medium | | high | | | 04 2.01 mm | 05 3.29 mm | 04 2.47 mm |
| 30° C./mm | | | low | | medium | | high | | | 04 0.91 mm | 07 2.17 mm | 05 1.23 mm |
| Morphological property | | | | | | | | | | | | |
| Cap | | | | | | | | | | | | |
| Cross sectional shape | convex | round (rounded) | flat | concave | | | | | other | 02 | 02 | 02 |

TABLE 2-continued

Fungus characteristics Table of *Hypsizygus marmoreus* (Peck) H.E. Bigelow of Recording and Registration
(Please circle the applicable items for the characteristics.)

| Character | Characteristic values of present variety (comparison with standard varieties) 01 | 02 | 03 | 04 | 05 | 06 | 07 | 08 | 09 | Remarks (Measured values, etc.) | Characteristic values of similar varieties (marmo22go) | (Hokuto 18gokin) |
|---|---|---|---|---|---|---|---|---|---|---|---|---|
| Mottle of the surface | few | medium | many | | | | | | | 02 | 02 | 02 |
| Size of mottle | small | medium | large | | | | | | | 03 | 01 | 03 |
| Distribution of mottle | center part | whole part | | | | | | | | 01 | 02 | 02 |
| Clarity of mottle | unclarity | moderate | clarity | | | | | | | 03 | 03 | 03 |
| Size | | | small | | medium | | large | | | 03<br>21.2 mm | 03<br>23.2 mm | 02<br>20.4 mm |
| Color of central area | white | grey-yellow | light grey-brown | yellow-brown | light brown | dark tan | dark grey tan | dark grey brown | other | 05<br>199A | 05<br>199C | 05<br>199B |
| Color of peripheral area | white | grey-yellow | light grey-brown | yellow-brown | light brown | dark tan | dark grey tan | dark grey brown | other | 05<br>199C | 05<br>199D | 05<br>199D |
| Thickness | | | thin | | medium | | thick | | | 08<br>9.8 mm | 09<br>11.3 mm | 0.7<br>8.1 mm |
| Fleshy | | | soft | | medium | | hard | | | 05 | 05 | 07 |
| **Gill** | | | | | | | | | | | | |
| Color | white | yellow-white | light orange yellow | grey-yellow | | | | | other | 02<br>158C | 02<br>158C | 02<br>158C |
| Alignment | normal | very irregular | | | | | | | other | 02 | 02 | 02 |
| Width | narrow | medium | wide | | | | | | | 02 | 02 | 02 |
| Density | low | Medium | high | | | | | | | 02 | 02 | 02 |
| **Stipe** | | | | | | | | | | | | |
| Shape | long and thin | short and thin | long and thick | short and thick | Medium | | | | | 05 | 05 | 01 |
| Length | | | short | | Medium | | long | | | 05<br>56.0 mm | 05<br>53.9 mm | 04<br>52.8 mm |
| Thickness | | | thin | | medium | | thick | | | 09<br>17.7 mm | 08<br>16.5 mm | 05<br>9.4 mm |
| Color | white | yellow-white | grey | grey-brown | | | | | other | 01<br>155B | 01<br>155B | 01<br>155B |
| Hair | absent | few | medium | many | | | | | | 01 | 01 | 01 |
| Fleshy | soft | medium | hard | | | | | | | 03 | 02 | 02 |

TABLE 2-continued

Fungus characteristics Table of *Hypsizygus marmoreus* (Peck) H.E. Bigelow of Recording and Registration
(Please circle the applicable items for the characteristics.)

| Character | Characteristic values of present variety (comparison with standard varieties) 01 | 02 | 03 | 04 | 05 | 06 | 07 | 08 | 09 | Remarks (Measured values, etc.) | Characteristic values of similar varieties (marmo22go) | (Hokuto 18gokin) |
|---|---|---|---|---|---|---|---|---|---|---|---|---|
| Ratio of maximum diameter of stem to diameter just below cap | | | small | | medium | | large | | | 07 2.24 | 06 1.91 | 04 1.52 |
| **Cultural property** | | | | | | | | | | | | |
| Development of fruit body | | | | | | | | | | | | |
| Development | group | scattered | stock | | | | | | | 03 | 03 | 03 |
| Optimal culture period | | | short | | Medium | | long | | | 05 80 days | 05 80 days | 06 90 days |
| Length of time from fruit body-formation promotion to fruit body harvesting | | | short | | Medium | | long | | | 05 23.3 days | 04 21.9 days | 05 22.3 days |
| Optimal temperature for primordial development | | | low | | medium | | high | | | 07 19° C. | 07 19° C. | 05 15° C. |
| Optimal temperature for fruit body growth | | | low | | Medium | | high | | | 05 15° C. | 05 15° C. | 05 15° C. |
| Adaptivity for illuminance | | | | | | | | | | | | |
| Adaptivity for culture | | | | | | | | | | | | |
| **Yield** | | | | | | | | | | | | |
| Yield of fruit body | | | few | | Medium | | many | | | 05 125.4 g | 06 137.0 g | 02 98.4 g |
| The number of productive stems | | | few | | medium | | many | | | 02 19.4 stems | 03 21.7 stems | 03 23.6 stems |
| **Other property** | | | | | | | | | | | | |
| Bitter ingredient | none | weak | strong | | | | | | | | | |
| Disease resistance | | | | | | | | | | | | |
| Ingredients | | | | | | | | | | | | |

Notes:
Circle shows the characteristics of 'HKHM25'.

The R.H.S. Colour Chart of The Royal Horticultural Society of London (R.H.S.), fifth edition published in 2007, The R.H.S. contact: R.H.S. Membership Department The Royal Horticultural Society PO Box 313 London, SW1P 2PE

What is claimed is:

1. A new, distinct variety of Bunashimeji Mushroom as substantially illustrated and described in the specification.

* * * * *